(12) United States Patent
Ueda et al.

(10) Patent No.: US 7,105,709 B2
(45) Date of Patent: Sep. 12, 2006

(54) METHOD OF PRODUCING REDUCED COENZYME Q10

(75) Inventors: Takahiro Ueda, Hyogo (JP); Shiro Kitamura, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 291 days.

(21) Appl. No.: 10/483,643

(22) PCT Filed: Jul. 15, 2002

(86) PCT No.: PCT/JP02/07147

§ 371 (c)(1),
(2), (4) Date: Jun. 1, 2004

(87) PCT Pub. No.: WO03/006412

PCT Pub. Date: Jan. 23, 2003

(65) Prior Publication Data

US 2004/0236154 A1    Nov. 25, 2004

(30) Foreign Application Priority Data

Jul. 13, 2001    (JP)    ............................. 2001-214482
Apr. 17, 2002    (JP)    ............................. 2002-114877

(51) Int. Cl.
*C07C 35/18*    (2006.01)
*C07C 50/04*    (2006.01)

(52) U.S. Cl. ....................... 568/823; 568/830; 552/293

(58) Field of Classification Search ..................... None
See application file for complete search history.

(56) References Cited

U.S. PATENT DOCUMENTS 6,184,255 B1    2/2001    Mae et al. .................. 514/720

FOREIGN PATENT DOCUMENTS

| JP | 53-133687 | 11/1978 |
| JP | 57-70834 | 5/1982 |
| JP | 60-75294 | 4/1985 |

OTHER PUBLICATIONS

International Search Report From Corresponding International Application No. PCT/JP02/07147, Dated Oct. 21, 2002, 1 page.
Patent Cooperation Treaty International Preliminary Examination Report (PCT Article 36 and Rule 70), From Corresponding International Application No. PCT/JP02/07147, Dated Feb. 27, 2003, 3 Pages.

*Primary Examiner*—Sikarl A. Witherspoon
(74) *Attorney, Agent, or Firm*—Brinks Hofer Gilson & Lione

(57) ABSTRACT

The present invention relates to a method of conveniently and efficiently producing high-quality reduced coenzyme $Q_{10}$ which is useful as an ingredient in foods, functional nutritive foods, specific health foods, nutritional supplements, nutrients, animal drugs, drinks, feeds, cosmetics, medicines, remedies, preventive drugs, etc. This method is suitable for industrial production thereof.

A method of producing a reduced coenzyme $Q_{10}$
which comprises reducing an oxidized coenzyme $Q_{10}$ in an aqueous medium with the use of dithionous acid or a salt thereof,
said reduction being carried out in the coexistence of a salt and/or under deoxygenated atmosphere, and at pH of 7 or below. Thus, the formation of the oxidized coenzyme $Q_{10}$ as a by-product due to oxidation can be minimized, thereby giving reduced coenzyme Q10 having excellent qualities in a high yield.

14 Claims, No Drawings

METHOD OF PRODUCING REDUCED COENZYME Q10

RELATED APPLICATIONS

This application is a nationalization of PCT Application No. PCT/JP02/07147 filed Jul. 15, 2002. This application claims priority from Japanese Patent Application No. 2001-214482 filed on Jul. 13, 2001 and Japanese Patent Application No. 2002-114877 filed on Apr. 17, 2002.

TECHNICAL FIELD

The present invention relates to a method of producing a reduced coenzyme $Q_{10}$. Reduced coenzyme $Q_{10}$ shows a higher level of oral absorbability as compared with oxidized coenzyme $Q_{10}$ and is a compound useful as an ingredient in good foods, functional nutritive foods, specific health foods, nutritional supplements, nutrients, animal drugs, drinks, feeds, cosmetics, medicines, remedies, preventive drugs, etc.

BACKGROUND ART

It is known that reduced coenzyme $Q_{10}$ can be prepared by producing coenzyme $Q_{10}$ in the conventional manner, for example by synthesis, fermentation, or extraction from natural products, and concentrating a reduced coenzyme $Q_{10}$-containing eluate fraction resulting from chromatography (JP-A-10-109933). On that occasion, as described in the above-cited publication, the chromatographic concentration may be carried out after reduction of oxidized coenzyme $Q_{10}$ contained in the reduced coenzyme $Q_{10}$ with a reducing agent such as sodium borohydride or sodium dithionite (sodium hyposulfite), or reduced coenzyme $Q_{10}$ may be prepared by reacting the reducing agent mentioned above with an existing highly pure grade of coenzyme $Q_{10}$.

JP-A-57-70834 discloses an example in which reduced coenzyme $Q_{10}$ was synthesized by dissolving coenzyme $Q_{10}$ in hexane and adding an aqueous solution of sodium hydrosulfite (sodium hyposulfite) in an amount of twice the weight of coenzyme $Q_{10}$ to the solution, followed by stirring.

However, the present inventors preliminary investigated the above reduction method, and found that it is not so easy to obtain a high-quality reduced coenzyme $Q_{10}$ in a high yield.

The above problem leads to not only economical disadvantageous but also to problems in qualities such as the immixture of oxidized coenzyme $Q_{10}$, which is difficult to remove, into a product. Moreover, use of a large amount of a reducing agent enhances the load for removal and detoxification of the reducing agent and components derived therefrom.

Thus, the above disadvantages in the reduction reaction give rise to a necessity of another process for purification.

SUMMARY OF THE INVENTION

In view of the foregoing, the present invention has an object to provide a convenient and efficient synthesis method to obtain high-quality reduced coenzyme $Q_{10}$.

The present inventors made intensive investigations, and as a result, found that high-quality reduced coenzyme $Q_{10}$ can be obtained at a high yield in a convenient and efficient manner, by carrying out a reduction reaction under specific condition in a method of producing reduced coenzyme $Q_{10}$ comprising reducing oxidized coenzyme $Q_{10}$ with dithionous acid or a salt thereof. Based on this finding, the present inventors have completed the present invention.

Accordingly, the present invention is a method of synthesizing a reduced coenzyme $Q_{10}$
which comprises reducing an oxidized coenzyme $Q_{10}$ in an aqueous medium with the use of dithionous acid or a salt thereof,
said reduction being carried out in the coexistence of a salt and/or under deoxygenated atmosphere, and at pH of 7 or below.

DETAILED DESCRIPTION OF THE INVENTION

Hereafter, the present invention is described in detail.

In the present invention, dithionous acid or a salt thereof is used as a reducing agent. The dithionous acid or a salt thereof is not particularly restricted but a salt form of dithionous acid is generally used. The salt of dithionous acid is not particularly restricted but includes, as preferred species, alkali metal salts, alkaline earth metal salts, ammonium salts and the like. Alkali metal salts such as a lithium salt, a sodium salt, and a potassium salt are more preferred, and a sodium salt is most preferred.

The above reduction reaction is carried out in an aqueous medium. The amount of water to be used in the reduction reaction is not particularly restricted, but may be an amount of water such that an appropriate amount of the reducing agent, namely dithionous acid or a salt thereof, can be dissolved therein. In general, for example, it is advisable that the amount of the dithionous acid or a salt be adjusted usually to not more than 30 w/w %, and preferably not more than 20 w/w %, relative to the weight of water. From the productivity viewpoint, among others, it is advisable that the amount be adjusted generally to not less than 1 w/w %, preferably not less than 5 w/w %, and more preferably not less than 10 w/w %.

The above reduction reaction is carried out in the coexistence of a salt and/or under deoxygenated atmosphere, and at pH of 7 or below. In other words, the above reduction reaction may be carried out under oxygen-containing atmosphere when under in the coexistence of a salt and at pH of 7 or below. Moreover, a condition with no existence of salts is allowable when the reduction is carried out under deoxygenated atmosphere and at pH of 7 or below. Furthermore, it is also possible to carry out the reduction in the existence of salt and under deoxygenated atmosphere, at pH of 7 or below.

The above salt is not particularly restricted as long as the reduced coenzyme $Q_{10}$ is not oxidized therewith. For example, there may be mentioned a salt constituted from an alkaline metal such as lithium, sodium and potassium, or alkaline earth metals such as magnesium and potassium, with a halogen atom such as fluorine, chloride and bromine, or a residue obtained by excluding a proton from an inorganic acid such as sulfuric acid or an organic acid such as formic acid, acetic acid and propionic acid. Among these, inorganic salts are preferred, and sodium chloride, potassium chloride, sodium sulfate, and the like are more preferred.

Regarding a concentration of the above salt, high concentration is preferable. Specifically, the concentration is preferably 3 w/w % or above, more preferably 5 w/w % or above, and still more preferably 10 w/w % or above, relative to water. Moreover, it is particularly preferable to dissolve the above salt in a reaction system (aqueous medium) so as to be saturation or close to saturation.

The above deoxygenated atmosphere can be attained by substitution with an inert gas, pressure reduction, boiling, or a combination of these. It is preferable to carry out at least the substitution with an inert gas, namely to use an inert gas atmosphere. As the inert gas, there may be mentioned, for example, nitrogen gas, carbon dioxide gas, helium gas, argon gas, hydrogen gas and the like. Nitrogen gas is preferred, however.

It was found that the reduction reaction in the coexistence of a salt and/or under deoxygenated atmosphere mentioned above was particularly effective when dithionous acid or a salt is used as a reducing agent, and that such a reaction greatly contributed to an improvement of the yield in the reduction reaction or decrease of the reducing agent.

Moreover, the above reduction reaction is carried out at pH of 7 or below, preferably at pH range of 3 to 7, and more preferably at pH range of 3 to 6. The above pH may be adjusted with acids (e.g. mineral acids such as hydrochloric acid and sulfuric acid) or bases (e.g. alkaline metal hydroxides such as sodium hydroxide).

As described above, various factors may be appropriately controlled for minimizing a residence of oxidized coenzyme $Q_{10}$ or a formation of the oxidized coenzyme $Q_{10}$ as a by-product from the reduced coenzyme $Q_{10}$, and thus high-quality reduced coenzyme $Q_{10}$ may be synthesized in a high yield.

In the above reduction reaction, preferable environment are provided, which enable the reduction reaction to preferably proceed, and residence, by-product formation and immixture of the oxidized coenzyme $Q_{10}$ to minimize. Therefore, high yield maybe stably attained. Moreover, it is also possible to minimize the amount of the above hyposulfurous acid or salt to be used as a reducing agent.

In the above reduction reaction, preferable environment are provided, which enable the reduction reaction to preferably proceed, and residence, by-product formation and immixture of the oxidized coenzyme $Q_{10}$ to minimize. Therefore, high yield may be stably attained. Moreover, it is also possible to minimize the amount of the above dithionous acid or salt to be used as a reducing agent.

The amount of the dithionous acid or salt to be used is not particularly restricted. From the economical viewpoint, however, the amount to be used may be not larger than the charged weight of oxidized coenzyme $Q_{10}$. The lower limit may be preferably not smaller than about $1/5$ by weight, more preferably not smaller than about $2/5$ by weight, and still more preferably not smaller than about $3/5$ by weight, based on the charged weight of oxidized coenzyme $Q_{10}$. Thus, the reaction can be more favorably carried out with an amount within the range of about $2/5$ by weight of the above-mentioned charged weight to a weight roughly equal to that of the charged weight.

The temperature for the above reduction reaction is not particularly restricted, but preferably 100° C. or below, more preferably80° C. or below, and still more preferably 60° C. or below. The lower limit of the temperature is preferably the solidification temperature of the system. The reaction may be preferably carried out at a temperature range of 0 to 100° C., more preferably at 0 to 80° C., and still more preferably at 0 to 60° C.

The substrate concentration in the above reduction reaction is not particularly restricted but the weight of oxidized coenzyme $Q_{10}$ relative to the solvent weight is preferably not less than 1 w/w %, more preferably not less than 3 w/w %, still more preferably not less than 10 w/w %, and particularly preferably not less than 15 w/w %. The upper limit is not particularly restricted, too, but is preferably not more than about 60 w/w %, more preferably not more than 50 w/w %, still more preferably,not more than 40 w/w %, and particularly preferably not more than 30 w/w %. Thus, the reaction can be favorably carried out at a substrate concentration of about 1 to 60 w/w %, preferably about 3 to 50 w/w %, and more preferably about 10 to 40 w/w %.

The above reduction reaction is carried out in an aqueous medium. The aqueous medium may be simple water, or may be a combination of water and an organic solvent.

The above organic solvent is not particularly restricted, but preferably at least one species selected from hydrocarbons, fatty acid esters, ethers and nitriles in view of the yield and qualities of the reduced coenzyme $Q_{10}$, and among them, hydrocarbons are preferred. The above organic solvents are effective solvents having great ability to inhibit residence, by-products formation and immixture of the oxidized coenzyme $Q_{10}$.

The hydrocarbons are not particularly restricted, but there may be mentioned, for example, aliphatic hydrocarbons, aromatic hydrocarbons, halogenated hydrocarbons, etc. Preferred are aliphatic hydrocarbons and aromatic hydrocarbons, and, among them, aliphatic hydrocarbons are particularly preferred.

The aliphatic hydrocarbons are not particularly restricted, and may be cyclic or acyclic, or saturated or unsaturated. However, generally they contain 3 to 20 carbon atoms, and preferably 5 to 12 carbon atoms.

As specific examples, there may be mentioned, for example, propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, etc.

Among them, saturated aliphatic hydrocarbons having 5 to 8carbon atoms are more preferred, and preferably used are pentane, 2-methylbutane and cyclopentane, which have 5 carbon atoms (referred to as "pentanes"); hexane, 2-methylpentane, 2,2-dimethylbutane, 2,3-dimethylbutane, methylcyclopentane, cyclohexane, which have 6 carbon atoms (referred to as "hexanes"); heptane, 2-methylhexane, 3-methylhexane, 2,3-dimethylpentane, 2,4-dimethylpentane, methylcyclohexane, which have 7 carbon atoms (referred to as "heptanes"); octane, 2,2,3-trimethylpentane, isooctane, ethylcyclohexane, which have 8 carbon atoms (referred to as octanes); and a mixture of these. In particular, the above heptanes are particularly preferred since they have a tendency to show a very high effect to protect reduced coenzyme $Q_{10}$ from oxidization, and heptane is most preferred.

The aromatic hydrocarbons are not particularly restricted, but generally they contain 6 to 20 carbon atoms, preferably 6 to 12 carbon atoms, and more preferably 7 to 10 carbon atoms. As specific examples, there may be mentioned, for example, benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, etc. Preferred are toluene, xylene, o-xylene, m-xylene, p-xylene, ethylbenzene, cumene, mesitylene, tetralin, butylbenzene, p-cymene, cyclohexylbenzene, diethylbenzene and pentylbenzene. More preferred are toluene, xylene, o-xylene, m-xylene, p-xylene, cumene and tetralin, and most preferred is cumene.

The halogenated hydrocarbons are not particularly restricted, and may be cyclic or acyclic, or saturated or unsaturated. However, acyclic halogenated hydrocarbons are preferably used. More preferred are chlorinated hydrocarbons and fluorinated hydrocarbons, and chlorinated hydrocarbons are still more preferred. Additionally, ones containing 1 to 6 carbon atoms, preferably 1 to 4 carbon atoms, and more preferably 1 to 2 carbon atoms are used.

As specific examples, for example, there maybe mentioned dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane, etc.

Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene and 1,1,1,2-tetrafluoroethane. More preferred are dichloromethane, chloroform, 1,2-dichloroethylene, trichloroethylene, chlorobenzene and 1,1,1,2-tetrafluoroethane.

The fatty acid esters are not particularly restricted, but there maybe mentioned, for example, propionates, acetates, formates, etc. Preferred are acetates and formates, and more preferred are acetates. Ester functional groups thereof are not particularly restricted, but alkyl esters having 1 to 8 carbon atoms, aralkyl esters having 1 to 8 carbon atoms, preferred are alkyl esters having 1 to 6 carbon atoms, and more preferred are alkyl esters having 1 to 4 carbon atoms are used.

As the propionates, there may be mentioned, for example, methyl propionate, ethyl propionate, butyl propionate, isopentyl propionate, etc.

As the acetates, there may be mentioned, for example, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, etc. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate and cyclohexyl acetate. More preferred are methyl acetate, ethyl acetate, propyl acetate, isopropyl acetate, butyl acetate and isobutyl acetate. Most preferred is ethyl acetate.

As the formates, there may be mentioned, for example, methyl formate, ethyl formate, propyl formate, isopropyl formate, butyl formate, isobutyl formate, sec-butyl formate, pentyl formate, etc. Preferred are methyl formate, ethyl formate, propyl formate, butyl formate, isobutyl formate and pentyl formate, and most preferred is ethyl formate.

The ethers are not particularly restricted, and may be cyclic or acyclic, or saturated or unsaturated. But saturated ones are preferably used. Generally, ones containing 3 to 20 carbon atoms, and preferably 4 to 12 carbon atoms and more preferably 4 to 8 carbon atoms are used.

As specific examples, there may be mentioned, for example, diethyl ether, methyl tert-butyl ether, dipropyl ether, diisopropyl ether, dibutyl ether, dihexyl ether, ethyl vinyl ether, butyl vinyl ether, anisol, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether, etc.

Preferred are diethyl ether, methyl tert-butyl ether, dipropyl ether, diisopropyl ether, dibutyl ether, dihexyl ether, anisol, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether. More preferred are diethyl ether, methyl tert-butyl ether, anisol, dioxane, tetrahydrofuran, ethylene glycol monomethyl ether and ethylene glycol monoethyl ether. More preferred are diethyl ether, methyl tert-butyl ether, anisol, etc., and most preferred is methyl tert-butyl ether.

The nitriles are not particularly restricted, and may be cyclic or acyclic, or saturated or unsaturated. However, saturated ones are preferably used. Generally, ones containing 2 to 20 carbon atoms, preferably 2 to 12 carbon atoms, and more preferably 2 to 8 carbon atoms are used.

As specific examples, there may be mentioned, for example, acetonitrile, propiononitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropiononitrile, bromopropiononitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropiononitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, tolylcyclohexanecarbonitrile, etc.

Preferred are acetonitrile, propiononitrile, succinonitrile, butyronitrile, isobutyronitrile, valeronitrile, methyl cyanoacetate, ethyl cyanoacetate, benzonitrile, tolunitrile and chloropropiononitrile. More preferred are acetonitrile, propiononitrile, butyronitrile and isobutyronitrile, and most preferred is acetonitrile.

Among the above organic solvents, it is preferred to use a solvent with low miscibility to water. This makes it possible to adequately carry out the above reduction reaction and, additionally, post-treatments after the reduction reaction.

In selecting the solvent to be used from among the solvents mentioned above, such properties as boiling point and viscosity are preferably taken into consideration; for example, the solvent should have a boiling point which allows appropriate warming for increasing the solubility and facilitates solvent recovery from crystallization filtrates and a solvent removal from wet masses by drying (about 30 to 150° C. at 1 atm), a melting point such that solidification hardly occurs in handling at room temperature as well as upon cooling to room temperature or below (not lower than about 0° C., preferably not lower than about 10° C., still more preferably not lower than about 20° C.), and a low viscosity (not higher than about 10 cp at 20° C.). From the industrial operation viewpoint, a solvent which is hardly volatile at ordinary temperature is preferred; generally, for example, one having a boiling point of not lower than about 80° C. is preferred, and one having a boiling point of not lower than about 90° C. is particularly preferred.

The above reduction reaction can be driven to completion usually within 5 hours, preferably within 3 hours, and more preferably within 1 hour.

The generated reduced coenzyme $Q_{10}$ is extracted into an organic solvent from thus-obtained aqueous mixture after the reduction reaction to recover an organic phase containing the reduced coenzyme $Q_{10}$. Then, if necessary (preferably), said organic phase is further washed with water repeatedly to completely remove impurities. The water to be used for washing is not particularly restricted, but preferably water or an aqueous solution containing a salt, preferably an inorganic salt such as sodium chloride, potassium chloride and sodium sulfate, etc. in view of easiness of liquid separation (wherein, concentration of the salt is preferably high, and it is usually 5 w/w % or above, preferably about 10 w/w % or above, and more preferably a concentration of saturation or close to saturation). The extraction and washing mentioned above may be carried out under acidic condition, preferably at pH of 6 or below, and more preferably at pH of 5 or below for minimizing the formation of oxidized coenzyme $Q_{10}$ as a by-products.

The organic solvent to be used for the extraction mentioned above is not particularly restricted. But from the fore mentioned viewpoints, it is preferable to use one species selected from hydrocarbons, fatty acid esters, ethers and nitriles as mentioned above. When the organic solvent is used together in the above reduction reaction, the same organic solvent is preferably used also as an extraction solvent.

The thus-obtained organic phase containing the reduced coenzyme $Q_{10}$ may be then subjected to operations appropriately combined among cooling, concentration, solvent substitution or the like, thereby crystallizing reduced coenzyme $Q_{10}$. The high-quality reduced coenzyme $Q_{10}$ recovered by the above method may be dried under normal pressure or reduced pressure.

The above-mentioned treatments after the reduction reaction, namely a series of operation from extraction to recovering dried crystal, are carried out under deoxygenated atmosphere. Preferably, the treatment may be carried out, for example, under inert gas atmosphere such as nitrogen gas, helium gas, carbon dioxide gas, argon gas and hydrogen gas atmosphere, and particularly preferably under nitrogen gas atmosphere.

In accordance with the present invention, various factors to inhibit residence, by-product formation and immixture of the oxidized coenzyme $Q_{10}$ can be appropriately controlled, and thus high-quality reduced coenzyme $Q_{10}$ may be obtained in a convenient and efficient manner at a high yield. The reduced coenzyme $Q_{10}$ as obtained in accordance with the present invention is a product with exceedingly high-quality, and can be expected to have a reduced coenzyme $Q_{10}$/oxidized coenzyme $Q_{10}$ weight ratio of not lower than 96/4, preferably not lower than 98/2, more preferably not lower than 99/1.

BEST MODE FOR CARRYING OUT THE INVENTION

The following examples illustrate the present invention in further detail. These examples are, however, by no means limitative of the scope of the present invention. In the examples, the purity of reduced coenzyme $Q_{10}$ and the reduced coenzyme $Q_{10}$/oxidized coenzyme $Q_{10}$ weight ratio were determined by the HPLC analysis specified below. The reduced coenzyme $Q_{10}$ purity values as determined, however, are by no means indicative of the limit purity value attainable in accordance with the present invention. Likewise, the reduced coenzyme $Q_{10}$/oxidized coenzyme $Q_{10}$ weight ratio values obtained never indicate the upper limit to that ratio.

(HPLC Conditions) Column: SYMMETRY C18 (product of Waters), 250 mm (in length), 4.6 mm (in inside diameter); mobile phase: $C_2H_5OH:CH_3OH=4:3$ (v/v); detection wavelength: 210 nm; flow rate: 1 ml/min; retention time of reduced coenzyme $Q_{10}$: 9.1 min; retention time of oxidized coenzyme $Q_{10}$: 13.3 min.

EXAMPLE 1

While stirring (stirring power consumption 0.3 kW/m$^3$), 100 g of the oxidized coenzyme $Q_{10}$ (purity 99.4%) at 48° C., a aqueous solution prepared by dissolving 80 g of sodium dithionite (purity 75% or more) in 1100 g of 10 w/w % brine was gradually added as a reducing agent, to carry out a reduction reaction at 48° C. and pH of 4 to 6. After the lapse of 2 hours, 1000 g of heptane was added thereto and an aqueous phase was removed. Then, a heptane phase was washed for 6 times with 1000 g of saturated brine adjusted to pH of 3 by hydrochloric acid, to give a heptane solution of the reduced coenzyme $Q_{10}$. All the above operations were carried out under nitrogen atmosphere. The weight ratio of the reduced coenzyme $Q_{10}$/oxidized coenzyme $Q_{10}$ in the heptane solution was 99.5/0.5, and the yield of the reduced coenzyme $Q_{10}$ was 99% by mole.

EXAMPLE 3

A heptane solution of reduced coenzyme $Q_{10}$ was obtained by the same procedure as in Example 1 except that an aqueous solution (no sodium chloride added) prepared by dissolving 80 g of sodium dithionite (purity 75% or more) in 1000 g of water was used as a reducing agent. The weight ratio of reduced coenzyme $Q_{10}$/oxidized coenzyme $Q_{10}$ in the heptane solution was 99.4/0.6, and the yield of the reduced coenzyme $Q_{10}$ was 99% by mole.

COMPARATIVE EXAMPLE 1

A heptane solution of the reduced coenzyme $Q_{10}$ was obtained by the same procedure as in Example 1 except that an aqueous solution (no sodium chloride added) prepared by dissolving 80 g of sodium dithionite (purity 75% or more) in 1000 g of water was used as a reducing agent and the reduction reaction was carried out in the atmosphere. The weight ratio of reduced coenzyme $Q_{10}$/oxidized coenzyme $Q_{10}$ in the heptane solution was 87.4/12.6, and the yield of the reduced coenzyme $Q_{10}$ was 87% by mole.

Oxidized coenzyme $Q_{10}$ (100 g; purity 99.4%) was dissolved in 1000 g of heptane at 25° C. While stirring (stirring power consumption 0.3 kW/m$^3$), an aqueous solution prepared by dissolving 62 g of sodium dithionite (purity 75% or more) in 1100 g of 10 w/w % brine was gradually added as a reducing agent, to carry out the reduction reaction at 25° C. and pH of 4 to 6. After the lapse of 2 hours, an aqueous phase was removed from the reaction solution, and a heptane phase was washed for 6 times with 1000 g of saturated brine adjusted to pH of 3 by hydrochloric acid, to give a heptane solution of reduced coenzyme $Q_{10}$. All the above operations were carried out under nitrogen atmosphere. The weight ratio of reduced coenzyme $Q_{10}$/oxidized coenzyme $Q_{10}$ in the heptane solution was 99.5/0.5, and the yield of the reduced coenzyme $Q_{10}$ was 99% by mole.

EXAMPLE 5

A heptane solution of the reduced coenzyme $Q_{10}$ was obtained by the same procedure as in Example 4 except that the reduction reaction was carried out in the atmosphere. The weight ratio of the reduced coenzyme $Q_{10}$/oxidized coenzyme $Q_{10}$ in the heptane solution was 99.3/0.7, and the yield of the reduced coenzyme $Q_{10}$ was 99% by mole.

EXAMPLE 6

A heptane solution of the reduced coenzyme $Q_{10}$ was obtained by the same procedure as in Example 4 except that an aqueous solution (no sodium chloride added) prepared by dissolving 62 g of sodium dithionite (purity 75% or more) in 1000 g of water was used as a reducing agent. The weight ratio of the reduced coenzyme $Q_{10}$/oxidized coenzyme $Q_{10}$ in the heptane solution was 99.4/0.6, and the yield of the reduced coenzyme $Q_{10}$ was 99% by mole. mole.

EXAMPLE 7

A hexane solution of reduced coenzyme $Q_{10}$ was obtained by the same procedure as in Example 5 except that hexane was used as a solvent for dissolving the oxidized coenzyme $Q_{10}$. The weight ratio of reduced coenzyme $Q_{10}$/oxidized coenzyme $Q_{10}$ in the hexane solution was 99.1/0.9, and the yield of reduced coenzyme $Q_{10}$ was 99% by mole.

COMPARATIVE EXAMPLE 2

A heptane solution of the reduced coenzyme $Q_{10}$ was obtained by the same procedure as in Example 4 except that an aqueous solution (no sodium chloride added) prepared by dissolving 62 g of sodium dithionite (purity 75% or more) in 1000 g of water was used as a reducing agent and the reduction reaction was carried out in the atmosphere. The weight ratio of reduced coenzyme $Q_{10}$/oxidized coenzyme $Q_{10}$ in the heptane solution was 91.0/9.0, and the yield of the reduced coenzyme $Q_{10}$ was 91% by mole.

EXAMPLE 8

A hexane solution of reduced coenzyme $Q_{10}$ was obtained by the same procedure as in Example 4 except that hexane was used as a solvent for dissolving oxidized coenzyme $Q_{10}$ and a solution (no sodium chloride added) dissolving 60 g of sodium dithionite (purity 75% or more) in 1000 g of water was used as a reducing agent. The weight ratio of reduced coenzyme $Q_{10}$/oxidized coenzyme $Q_{10}$ in the hexane solution was 99.3/0.7, and the yield of the reduced coenzyme $Q_{10}$ was 99% by mole.

COMPARATIVE EXAMPLE 3

A heptane solution of reduced coenzyme $Q_{10}$ was obtained by the same procedure as in Example 8 except that reduction reaction was carried out in the atmosphere. The weight ratio of reduced coenzyme $Q_{10}$/oxidized coenzyme $Q_{10}$ in the heptane solution was 90.9/9.1, and yield of the reduced coenzyme $Q_{10}$ was 91% by mole.

EXAMPLE 9

A heptane solution of the reduced coenzyme $Q_{10}$ was obtained by the same procedure as in Example 1 except that an aqueous solution prepared by dissolving 80 g of sodium dithionite (purity 75% or more) in 1050 g of 5 w/w % brine was used as a reducing agent and the reduction reaction was carried out in the atmosphere. The weight ratio of reduced coenzyme $Q_{10}$/oxidized coenzyme $Q_{10}$ was 98.9/1.1, and the yield of the reduced coenzyme $Q_{10}$ was 99% by mole.

COMPARATIVE EXAMPLE 4

A heptane solution of reduced coenzyme $Q_{10}$ was obtained by the same procedure as in Example 4 except that the reduction reaction was carried out at pH range of 8 to 9. The weight ratio of reduced coenzyme $Q_{10}$/oxidized coenzyme $Q_{10}$ in the heptane solution was 54.0/46.0, and the yield of the reduced coenzyme $Q_{10}$ was 54% by mole.

REFERENCE EXAMPLE 1

One gram of reduced coenzyme $Q_{10}$ (weight ratio of reduced coenzyme $Q_{10}$/oxidized coenzyme $Q_{10}$ is 99.6/0.4) was dissolved in 20 g of various solvents shown in Table 1 at 25° C. In the atmosphere, the weight ratio of reduced coenzyme $Q_{10}$/oxidized coenzyme $Q_{10}$ in the solutions were measured after stirring for 24 hours at 35° C. The results are shown in Table 1.

TABLE 1

| Solvent | R |
| --- | --- |
| Heptane | 99.1/0.9 |
| Hexane | 98.7/1.3 |
| Toluene | 98.8/1.2 |
| Chloroform | 98.9/1.1 |
| Ethyl acetate | 98.9/1.1 |
| Methyl tert-butyl ether | 98.6/1.4 |
| Tetrahydrofuran | 98.5/1.5 |

R: Reduced coenzyme $Q_{10}$/Oxidized coenzyme $Q_{10}$ weight ratio

REFERENCE EXAMPLE 2

One gram of reduced coenzyme $Q_{10}$ (weight ratio of reduced coenzyme $Q_{10}$/oxidized coenzyme $Q_{10}$ is 99.6/0.4) was dissolved in 100 g of various solvents shown in Table 2 at 35° C. In the atmosphere, the weight ratio of reduced coenzyme $Q_{10}$/oxidized coenzyme $Q_{10}$ in the solutions were measured after stirring for 24 hours at 25° C. The results are shown in Table 2.

TABLE 2

| Solvent | R |
| --- | --- |
| Heptane | 96.7/3.3 |
| Ethyl acetate | 96.4/3.6 |
| Acetonitrile | 96.0/4.0 |

R: Reduced coenzyme $Q_{10}$/Oxidized coenzyme $Q_{10}$ weight ratio

INDUSTRIAL APPLICABILITY

Since the present invention has the constitution mentioned above, high-quality reduced coenzyme $Q_{10}$ may be obtained in a convenient and efficient manner. Thus, the method is suited for the industrial scale production.

The invention claimed is:

1. A method of producing a reduced coenzyme $Q_{10}$ which comprises reducing an oxidized coenzyme $Q_{10}$ in an aqueous medium with use of dithionous acid or a salt thereof, said reduction being carried out in the coexistence of a salt and/or under deoxygenated atmosphere, and at pH of 7 or below.

2. The method according to claim 1, wherein the salt is an inorganic salt.

3. The method according to claim 2, wherein a concentration of the salt in water is 3 w/w % or more.

4. The method according to claim 1, wherein the deoxygenated atmosphere is an inert gas atmosphere.

5. The method according to claim 1, wherein pH range is between 3 and 7.

6. The method according to claim 1, wherein the aqueous medium is a mixed medium comprising water and an organic solvent.

7. The method according to claim 6, wherein the organic solvent is at least one species selected from the group consisting of hydrocarbons, fatty acid esters, ethers and nitrites.

8. The method according to claim 6, wherein the organic solvent is a hydrocarbon.

9. The method according to claim 6, wherein the organic solvent is one of pentanes, hexanes, heptanes or octanes.

10. The method according to claim 6, wherein the organic solvent is one of heptanes.

11. The method according to any one of claims 7–10, wherein an organic phase containing the reduced coenzyme $Q_{10}$ is recovered by extracting the generated reduced coenzyme $Q_{10}$ into the organic solvent after the reduction reaction.

12. The method according to claim 1, wherein the extraction is carried out at pH of 6 or below.

13. The method according to claim 11, wherein the organic phase recovered by the extraction is further washed with water.

14. The method according to claim 1 which is carried out under deoxygenated atmosphere.

* * * * *